United States Patent
Kim et al.

(10) Patent No.: US 10,010,262 B2
(45) Date of Patent: Jul. 3, 2018

(54) IMPEDANCE MEASURING CIRCUIT

(71) Applicant: Kabushiki Kaisha Toshiba, Minato-ku, Tokyo (JP)

(72) Inventors: Sinnyoung Kim, Ota Tokyo (JP); Shinji Nakatsuka, Kamakura Kanagawa (JP); Daisuke Kurose, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 108 days.

(21) Appl. No.: 15/065,180

(22) Filed: Mar. 9, 2016

(65) Prior Publication Data
US 2017/0086702 A1    Mar. 30, 2017

(30) Foreign Application Priority Data
Sep. 30, 2015  (JP) .................... 2015-194361

(51) Int. Cl.
G01R 27/08    (2006.01)
A61B 5/053   (2006.01)
G01R 27/26    (2006.01)
G01R 27/14    (2006.01)

(52) U.S. Cl.
CPC ............ *A61B 5/053* (2013.01); *G01R 27/14* (2013.01); *G01R 27/26* (2013.01); *A61B 2560/0209* (2013.01)

(58) Field of Classification Search
CPC .. G01N 27/4175; G01N 11/16; G01N 27/228; G01N 33/007; G01N 15/1459; G01N 27/4163; A61B 2560/0431; A61B 2560/0462; A61B 5/0537; A61B 5/7282; A61B 5/0245; A61B 5/0809; A61B 5/0205; G01R 27/261; G01R 19/04; G01R 19/16571; G01R 19/003; G01R 19/0092; G01R 27/14; G01R 27/26; H04B 10/564; H04B 10/6931; H04B 1/0458; G06F 3/011; G06F 19/34; G06F 19/3431; H04L 27/0002; G01K 1/024
See application file for complete search history.

(56) References Cited

U.S. PATENT DOCUMENTS

| | | | | |
|---|---|---|---|---|
| 5,862,458 | A * | 1/1999 | Ishii | .................... H04B 1/0458 455/107 |
| 8,257,565 | B2 * | 9/2012 | Kawase | ............. G01N 27/4065 204/424 |
| 2002/0067190 | A1 * | 6/2002 | Miyazaki | ............... G01R 19/04 327/91 |
| 2006/0102476 | A1 | 5/2006 | Niwa et al. | |
| 2017/0097377 | A1 * | 4/2017 | Ogawa | ................... G01R 15/06 |

FOREIGN PATENT DOCUMENTS

| | | |
|---|---|---|
| JP | H03-045474 B2 | 7/1991 |
| JP | H07-067066 B2 | 7/1995 |
| JP | 2000-065878 A | 3/2000 |
| JP | 2003-107026 A | 4/2003 |

* cited by examiner

*Primary Examiner* — Vinh Nguyen
(74) *Attorney, Agent, or Firm* — White & Case LLP

(57) ABSTRACT

An impedance measuring circuit has an amplification circuit connected to a target and to amplify a predetermined input signal with a gain corresponding to an impedance in the target and to output an output signal, a peak hold circuit to hold a peak value of the output signal and to output a hold value, and an impedance calculation circuit to calculate the impedance in the target based on the hold value.

9 Claims, 17 Drawing Sheets

(COMPARATIVE EXAMPLE)

FIG. 6 (COMPARATIVE EXAMPLE)

IMPEDANCE MEASURING CIRCUIT

CROSS REFERENCE TO RELATED APPLICATIONS

This application is based upon and claims the benefit of priority from the prior Japanese Patent Application No. 2015-194361, filed on Sep. 30, 2015, the entire contents of which are incorporated herein by reference.

FIELD

An embodiment of the present invention relates to an impedance measuring circuit.

BACKGROUND

Recently, impedance measuring circuits have been known where input signals such as AC signals are input to a target such as a living body and impedance in the target is measured based on a magnitude of the input signal attenuated after passing the target. Also, by detecting a change in the magnitude of the input signal after passing the target, a change in the impedance in the target can also be measured. When a living body is the target, it is desirable to measure a change of, for example, 1Ω or less in the impedance and thus an amplitude of the input signal is also limited to be relatively small. Therefore, it is desirable to measure a very small change in the amplitude.

In such an impedance measuring circuit, it is desired to reduce power consumption.

DETAILED DESCRIPTION

According to one embodiment, an impedance measuring circuit has an amplification circuit connected to a target and to amplify a predetermined input signal with a gain corresponding to an impedance in the target and to output an output signal, a peak hold circuit to hold a peak value of the output signal and to output a hold value, and an impedance calculation circuit to calculate the impedance in the target based on the hold value.

Embodiments of the present invention will be described below with reference to the drawings. These embodiments do not limit the present invention.

(First Embodiment)

Figure 1:
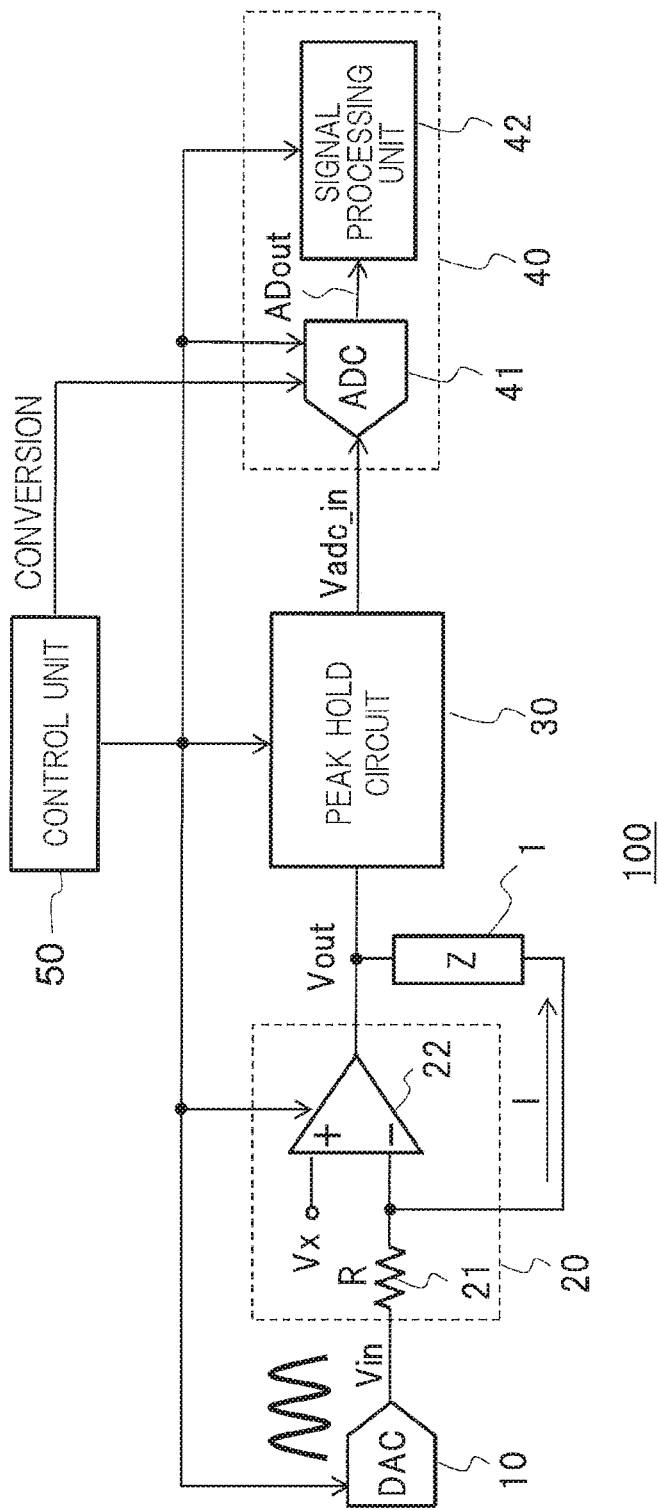
FIG. 1 is a block diagram illustrating an impedance measuring circuit according to a first embodiment.

FIG. 1 is a block diagram illustrating an impedance measuring circuit 100 according to a first embodiment. The impedance measuring circuit 100 measures an impedance Z of a target 1. The target 1 is not specifically limited as long as the target has conductivity. Here, an example of a living body such as a human body will be described.

The impedance measuring circuit 100 includes a DA converter 10, an amplification circuit 20, a peak hold circuit 30, an impedance calculation circuit 40, and a control unit 50. At least a part of the impedance measuring circuit 100 may be configured as a semiconductor integrated circuit.

The DA converter 10 performs DA conversion with a digital signal and generates a predetermined input signal Vin. The input signal Vin is, for example, an AC signal having a predetermined amplitude. A frequency of the AC signal is not specifically limited and may be, for example, 5 kHz to 200 kHz. A signal generating circuit other than the DA converter 10 may be used as long as the circuit is capable of generating the input signal Vin.

The amplification circuit 20 is connected to the target 1 and thereby amplifies the input signal Vin with a gain corresponding to the impedance Z of the target 1 and outputs an output signal Vout. The amplification circuit 20 includes a resistor 21 and a differential amplifier 22.

The resistor 21 has a resistance value of R and includes one end supplied with the input signal Vin.

The differential amplifier 22 includes an inverting input terminal (first input node) connected to another end of the resistor 21, a non-inverting input terminal (second input node) supplied with a predetermined reference voltage Vx, and an output terminal (output node) for outputting the output signal Vout after amplifying a difference between a voltage in the inverting input terminal and the reference voltage Vx.

The target 1 is connected between the inverting input terminal and output terminal of the differential amplifier 22. Therefore, an electric current I corresponding to the input signal Vin flows in the target 1.

The impedance Z of the target 1 can be expressed as $|Z|=|Vout|/|I|$. A value $|Vin|$ is known where $|I|=|Vin|/R$ holds. Therefore, a value $|I|$ is also known. Thus, measuring an amplitude of the output signal Vout allows for calculating the impedance Z. An amplitude of the output signal Vout is measured with a configuration below. Incidentally, for example, an amplitude of the input signal Vin and the resistance value R may be set such that the electric current I is less than 100 μA.

The peak hold circuit 30 holds a peak value of the output signal Vout and outputs a hold value Vadc_in. A peak value is a maximum value or a minimum value of the output signal Vout. An example will be described below where the maximum value is held; however, a case where the minimum value is held can also be configured in a similar manner.

The impedance calculation circuit 40 calculates the impedance Z of the target 1 based on the hold value Vadc_in held in the peak hold circuit 30, the amplitude of the input signal Vin, and the resistance value R.

The impedance calculation circuit 40 includes an AD converter 41 and a signal processing unit 42.

The AD converter 41 converts the hold value Vadc_in in the peak hold circuit 30 into a digital signal ADout when an AD conversion signal CONVERSION is given from the control unit 50. The AD converter 41 may be, for example, a ΔΣ AD converter with a relatively high resolution and relatively slow AD conversion. The AD converter 41 can measure a very small change in amplitude of, for example, less than 100 μV. This allows for measuring, for example, a change of 1Ω or less in the impedance Z even when amplitudes of the input signal Vin and electric current I are relatively small.

A frequency of the input signal Vin, which is an AC signal, is higher than a frequency that the AD converter 41 can perform AD conversion with. Therefore, the AD converter 41 cannot directly perform AD conversion with the output signal Vout. Thus, in the present embodiment, the hold value Vadc_in is converted into the digital signal ADout.

The signal processing unit 42 performs digital signal processing and thereby calculates the impedance Z based on the known electric current I and the digital signal ADout.

A specific configuration of the peak hold circuit 30 is not specifically limited. An example will be described below.

Figure 2A:
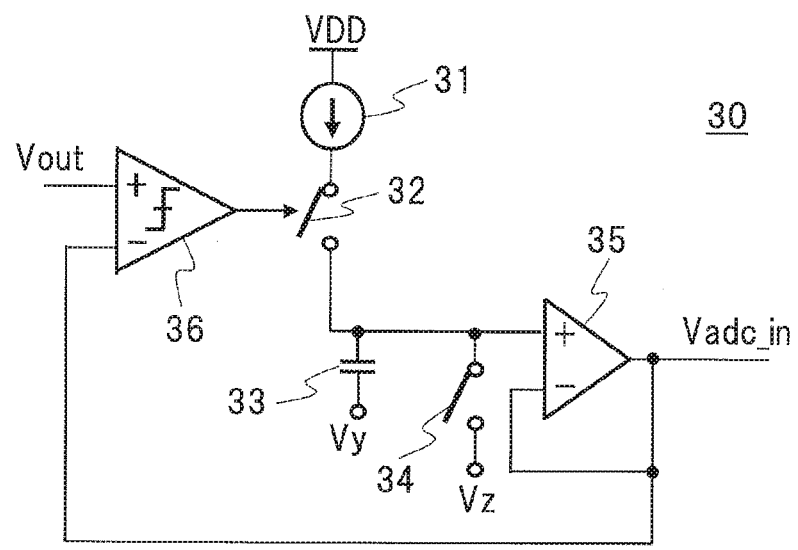
FIG. 2A is a circuit diagram illustrating a first example of a peak hold circuit in FIG. 1.

FIG. 2A is a circuit diagram illustrating a first example of the peak hold circuit 30 in FIG. 1. The peak hold circuit 30 is configured as a positive peak hold circuit and includes a first current source 31, a first switch 32, a first capacitor element 33, a reset switch 34, an amplifier 35, and a first comparator 36.

The first current source 31 is supplied with a power supply voltage VDD from one end thereof and outputs a constant first current from another end thereof. The first switch 32 is supplied with the first current from one end thereof.

The first capacitor element 33 is connected to another end of the first switch 32 and includes one end for holding a maximum value of the output signal Vout and another end supplied with the first voltage Vy. The first voltage Vy is a predetermined constant voltage.

The reset switch 34 includes one end connected to the one end of the first capacitor element 33 and another end supplied with a voltage Vz. The voltage Vz is smaller than an assumed minimum value of the maximum value of the output signal Vout. As a result, the reset switch 34 is turned on and a voltage in the one end of the first capacitor element 33 is initialized to the voltage Vz. Thereafter, the first capacitor element 33 can hold even the assumed minimum value of the maximum value of the output signal Vout.

The amplifier 35 includes a non-inverting input terminal connected to the one end of the first capacitor element 33, an inverting input terminal, and an output terminal connected to this inverting input terminal. The amplifier 35 functions as a buffer and outputs, from the output terminal thereof, the hold value Vadc_in equivalent to the maximum value held at the one end of the first capacitor element 33. The amplifier 35 may not be included and the maximum value held at the one end of the first capacitor element 33 may be output as the hold value Vadc_in.

The first comparator 36 includes a non-inverting input terminal supplied with the output signal Vout, an inverting input terminal supplied with the hold value Vadc_in, and an output terminal for controlling the first switch 32. The first comparator 36 turns on the first switch 32 when the output signal Vout is larger than or equal to the hold value Vadc_in. As a result, the first capacitor element 33 is charged with the first current. The first comparator 36 turns off the first switch 32 when the output signal Vout is smaller than the hold value Vadc_in. As a result, charging of the first capacitor element 33 is halted. Therefore, when the maximum value of the output signal Vout increases, the hold value Vadc_in increases and is renewed.

Figure 2B:
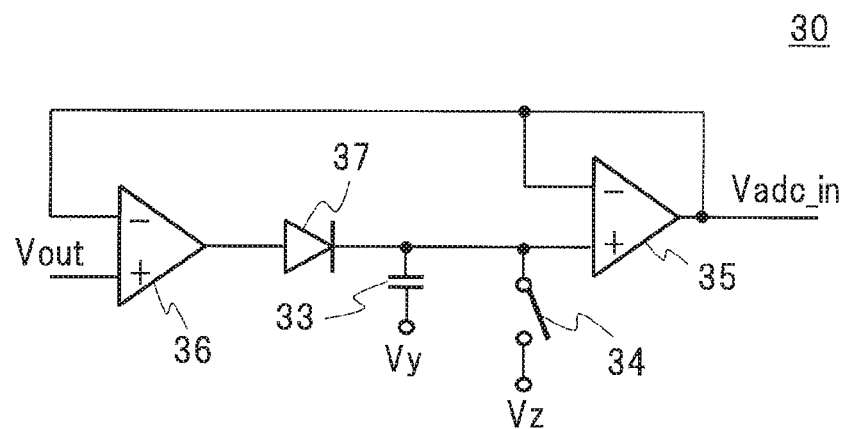
FIG. 2B is a circuit diagram illustrating a second example of the peak hold circuit in FIG. 1.

FIG. 2B is a circuit diagram illustrating a second example of the peak hold circuit 30 in FIG. 1. The peak hold circuit 30 includes a diode 37 instead of the first current source 31 and first switch 32, which is a point different from FIG. 2A. The diode 37 includes an anode connected to an output terminal of the first comparator 36 and a cathode connected to the one end of the first capacitor element 33.

The first comparator 36 increases a voltage in the output terminal and charges the first capacitor element 33 via the diode 37 when the output signal Vout is larger than or equal to the hold value Vadc_in. The first comparator 36 decreases the voltage in the output terminal and halts charging of the first capacitor element 33 when the output signal Vout is less than the hold value Vadc_in.

Such a configuration can also provide a similar function to that in FIG. 2A.

Figure 3A:
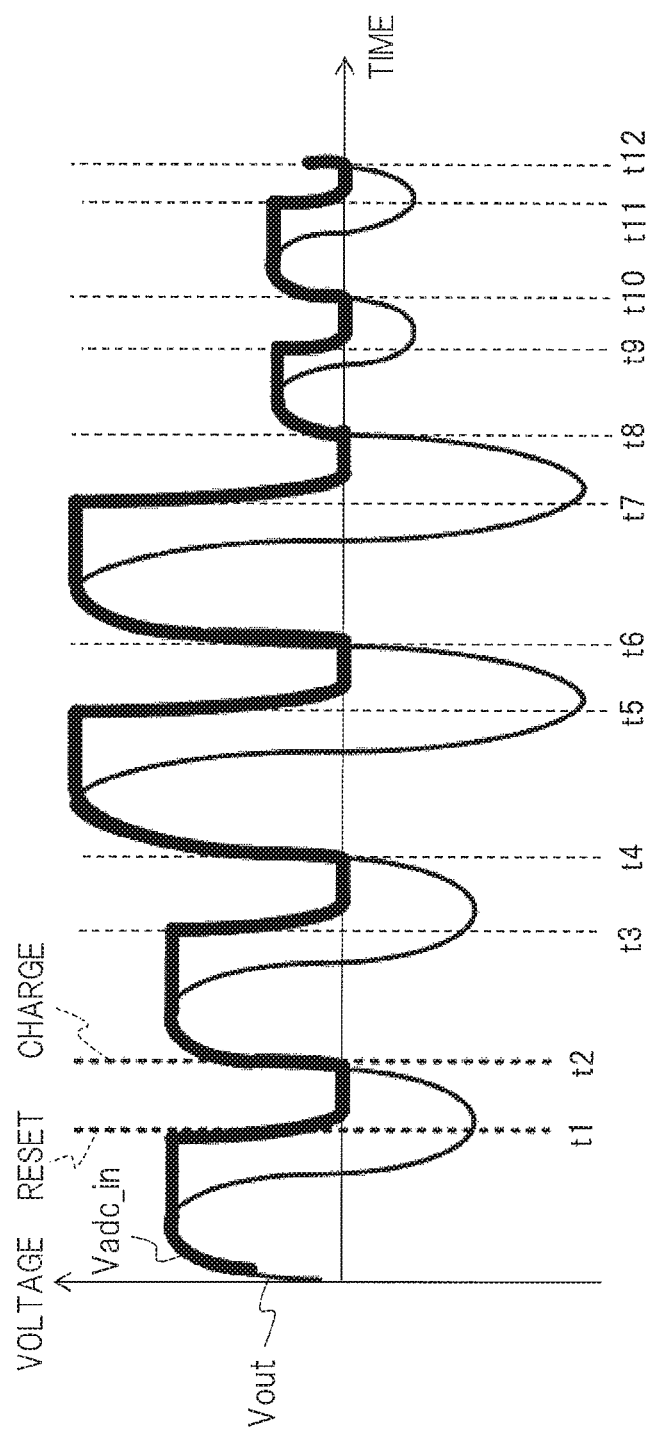
FIG. 3A is a waveform diagram illustrating a first example of an output signal Vout and a hold value Vadc_in of the impedance measuring circuit in FIG. 1.

FIG. 3A is a waveform diagram illustrating a first example of an output signal Vout and a hold value Vadc_in in the impedance measuring circuit 100 in FIG. 1. When measuring breathing speed of a living body based on the impedance Z, a change in the impedance Z is calculated. In order to decrease the hold value Vadc_in when the maximum value of the output signal Vout decreases due to the change in the impedance Z, the control unit 50 turns on the reset switch 34 for every predetermined reset timing (times t1, t3, t5, t7, t9, and t11) and resets (initializes) the hold value Vadc_in of the peak hold circuit 30. After every reset timing, the reset switch 34 is turned off after a predetermined period at charge timings (times t2, t4, t6, t8, t10, and t12) and holding a peak is initiated. The reset timing and charge timing are synchronized with the input signal Vin (that is, the output signal Vout). In the example illustrated, the reset timing and charge timing are set for every cycle of the output signal Vout.

After every charge timing, AD conversion can be performed before a subsequent reset timing. A timing for AD conversion is synchronized with the input signal Vin such that no AD conversion is performed between a reset timing and a subsequent charge timing.

Figure 3B:
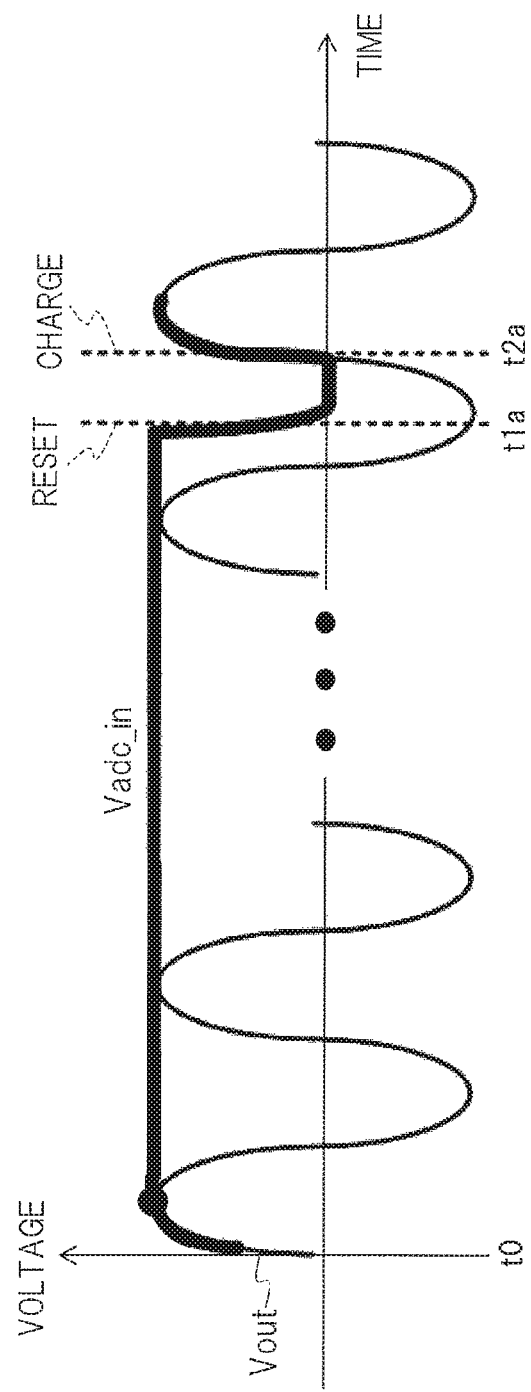
FIG. 3B is a waveform diagram illustrating a second example of the output signal Vout and hold value Vadc_in of the impedance measuring circuit in FIG. 1.

FIG. 3B is a waveform diagram illustrating a second example of an output signal Vout and a hold value Vadc_in of the impedance measuring circuit 100 in FIG. 1. When the impedance Z does not substantially vary for a certain period such as when body fat of a living body is measured based on the impedance Z, the maximum value of the output signal Vout does not substantially vary. Therefore, as illustrated in FIG. 3B, a peak can be held for a certain period from time t0 to time t1a that corresponds to a plurality of cycles of the input signal Vin and AD conversion can be performed during the period. A timing for AD conversion may not be synchronized with the input signal Vin. After resetting at the time t1a, holding a peak is initiated at a charge timing (time t2a) and a similar operation is repeated thereafter.

Figure 4:
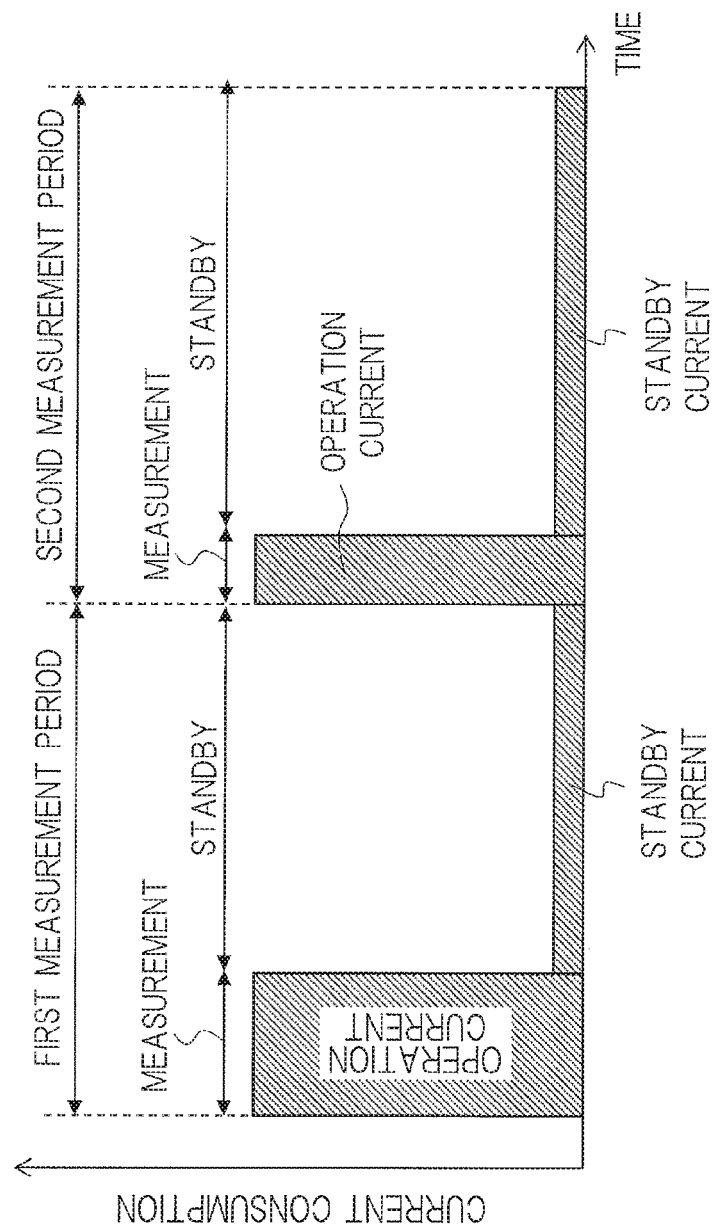
FIG. 4 is a diagram explaining intermittent operations of the impedance measuring circuit in FIG. 1.

FIG. 4 is a diagram explaining intermittent operations of the impedance measuring circuit 100 in FIG. 1. The control unit 50 causes the DA converter 10, amplification circuit 20, peak hold circuit 30, and impedance calculation circuit 40 to operate intermittently. As a result, as illustrated in FIG. 4, an operation current flows in the impedance measuring circuit 100 at the beginning of a first measurement period. As illustrated in FIG. 3A or 3B, AD conversion is then performed and the impedance Z is measured. Thereafter, the impedance measuring circuit 100 enters a standby state. The DA converter 10, amplification circuit 20, peak hold circuit 30, and impedance calculation circuit 40 halts operations thereof, where a standby current smaller than the operation current flows in the impedance measuring circuit 100. A similar operation is performed also in a subsequent second measurement period. Providing a standby period allows for reducing current consumption.

Here, a comparative example of an impedance measuring circuit 100X known to the present inventors will be described.

Figure 5:
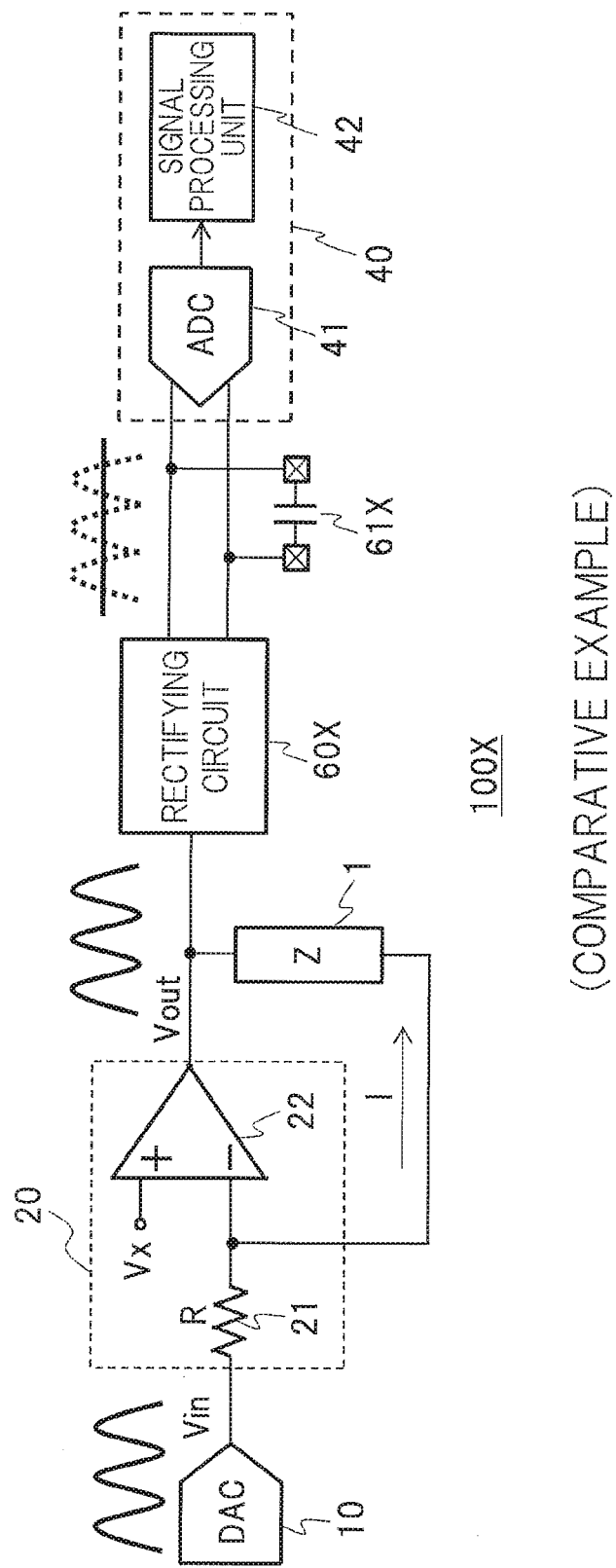
FIG. 5 is a block diagram illustrating a configuration of an impedance measuring circuit of a comparative example.

FIG. 5 is a block diagram illustrating a configuration of an impedance measuring circuit 100X of the comparative example. In FIG. 5, components common to those in FIG. 1 are denoted with the same signs as in FIG. 1. Different points are mainly described below.

The impedance measuring circuit 100X of the comparative example includes a rectifying circuit 60X and a capacitor element 61X instead of the peak hold circuit 30. The rectifying circuit 60X rectifies full waves of an output signal Vout. The capacitor element 61X smooths the signals subjected to full-wave rectification and supplies an obtained DC voltage to an AD converter 41. For sufficient smoothing, a capacitance value of the capacitor element 61X is relatively high. Although the AD converter 41 has a slow AD conversion speed as described above, AD conversion can be performed accurately with a DC voltage.

Figure 6:
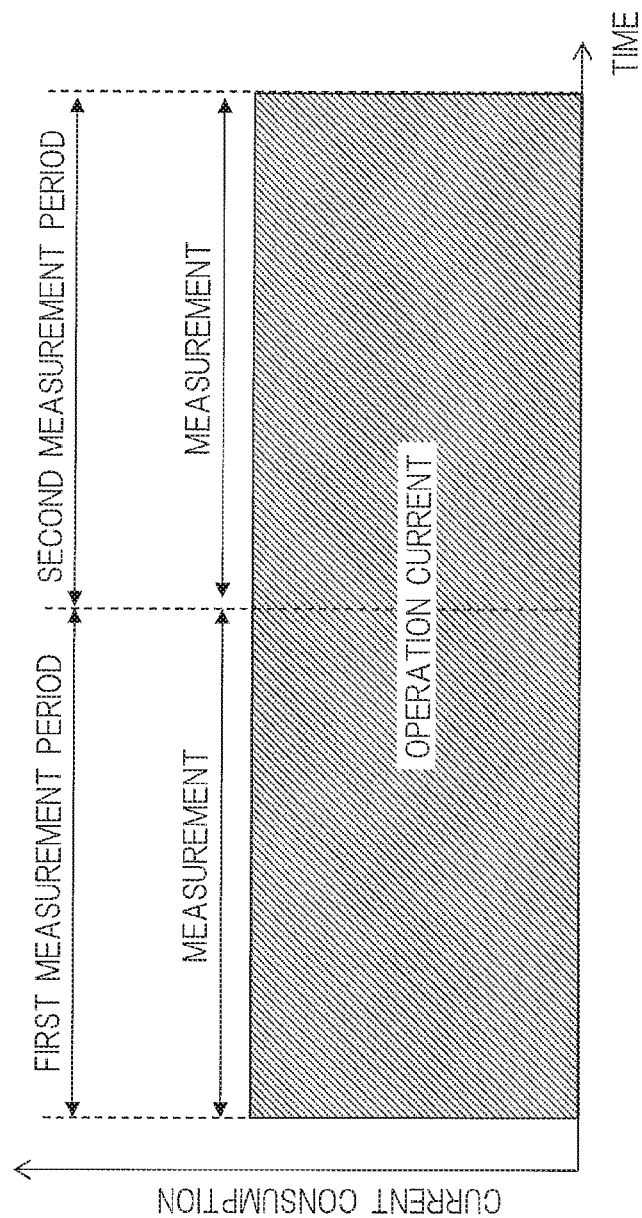
FIG. 6 is a diagram explaining current consumption of the impedance measuring circuit of the comparative example.

FIG. 6 is a diagram explaining current consumption of the impedance measuring circuit 100X of the comparative example. As illustrated in FIG. 6, an operation current flows in the impedance measuring circuit 100 during the entire first measurement period and the impedance Z is measured. A similar operation is performed also in a subsequent second measurement period.

The present inventors have uniquely found that, since the impedance measuring circuit 100X of the comparative example includes the capacitor element 61X of a large capacitance, when the operation is once halted, a relatively long time is required until a DC voltage supplied to the AD converter 41 is stabilized after the operation is restarted. Therefore, intermittent operations cannot be performed in an attempt to reduce current consumption. This is because intermittent operations require a long time for measurement of the impedance Z.

Contrary to this, in the present embodiment, the maximum value of the output signal Vout is held and the impedance Z of the target 1 is calculated based on the hold value Vadc_in. Since the hold value Vadc_in is stable, the impedance Z can be calculated using the impedance calculation circuit 40 including the AD converter 41 with a low AD conversion speed and a high resolution. Therefore, a small change in the impedance Z can be calculated with a high accuracy.

Furthermore, it is not required to smooth the output signal Vout as in the comparative example and the peak hold circuit 30 is only required to be capable of holding the maximum value of the output signal Vout. Thus, it is not required to include the capacitor element 61X of a large capacitance as in the comparative example. That is, a capacitance value of the first capacitor element 33 can be substantially smaller than the capacitance value of the capacitor element 61X of the comparative example. Therefore, the hold value Vadc_in supplied to the AD converter 41 is stabilized faster than in the comparative example upon intermittent operations. Therefore, power consumption can be reduced without deteriorating processing speed.

Incidentally, the input signal Vin may be a DC signal.
(Second Embodiment)

A second embodiment is different from the first embodiment in a point that conducts sample-hold of a value held as a peak.

Figure 7:
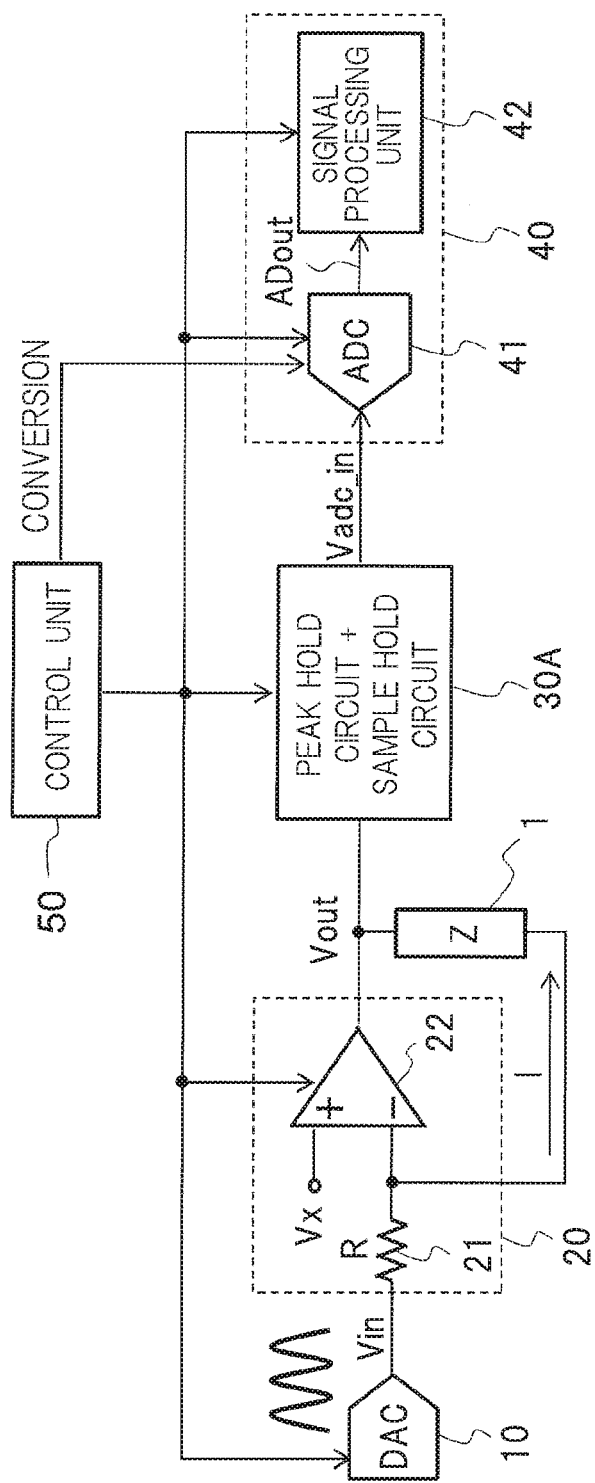
FIG. 7 is a block diagram illustrating an impedance measuring circuit according to a second embodiment.

FIG. 7 is a block diagram illustrating an impedance measuring circuit 100A according to the second embodiment. In FIG. 7, components common to those in FIG. 1 are denoted with the same signs as in FIG. 1. Different points are mainly described below. In the impedance measuring circuit 100A, a function of a peak hold circuit 30A is different as compared to the first embodiment. The peak hold circuit 30A holds a peak value (maximum value or minimum value) of an output signal Vout and conducts sample-hold of the peak value. A value obtained therefrom is then output as a hold value Vadc_in.

Figure 8:
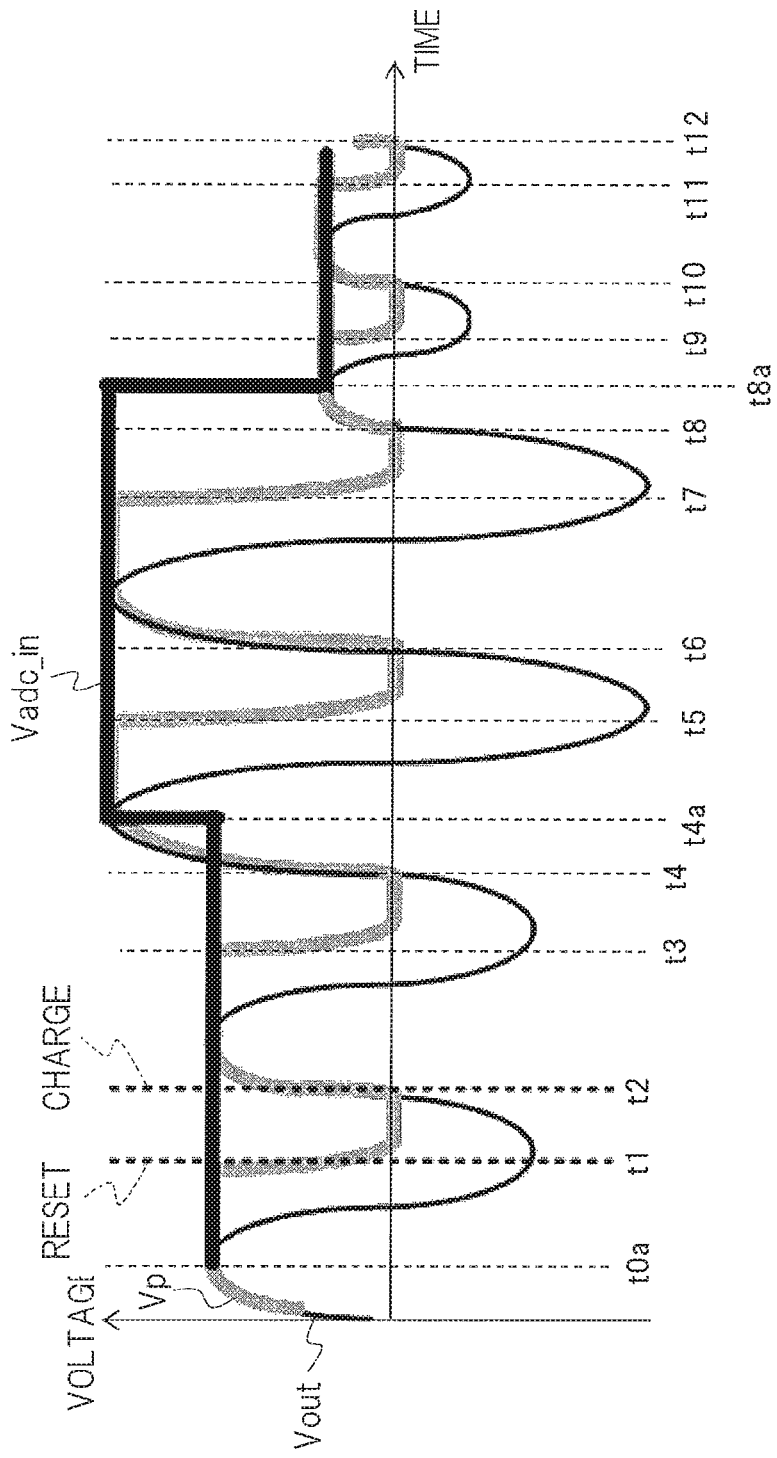
FIG. 8 is a waveform diagram illustrating an exemplary output signal Vout, maximum value Vp having been held, and hold value Vadc_in of the impedance measuring circuit in FIG. 7.

FIG. 8 is a waveform diagram illustrating an exemplary output signal Vout, maximum value Vp having been held, and hold value Vadc_in in the impedance measuring circuit 100A in FIG. 7. FIG. 8 illustrates an example where the output signal Vout is equivalent to that in FIG. 3A and the maximum value Vp, having been held, which is an internal signal of the peak hold circuit 30A, is equivalent to the hold value Vadc_in in FIG. 3A That is, a change in the impedance Z is calculated also in this case.

The peak hold circuit 30A conducts sample-hold of the maximum value Vp at each of times t0a, t4a, and t8a and then outputs as the hold value Vadc_in. As a result, even when the maximum value Vp, having been held, is reset during the times t0a to t4a corresponding to two cycles of the input signal Vin, the hold value Vadc_in is constant. Similarly, during each of the times t4a to t8a and times t8a to t12, the hold value Vadc_in is constant regardless of a change in the maximum value Vp having been held.

In this manner, since the hold value Vadc_in held by the sample-hold is constant during a predetermined number of cycles of the input signal Vin according to the present embodiment, AD conversion can be accurately performed even when a timing for AD conversion is not synchronized with the input signal Vin. Moreover, a value that has been reset can be caused not to be subjected to AD conversion.
(Influence of Low Frequency Noise in the First and Second Embodiments)

Here, prior to explanation on a third embodiment, influence of low frequency noise in the first and second embodiments will be described.

Figure 9A:
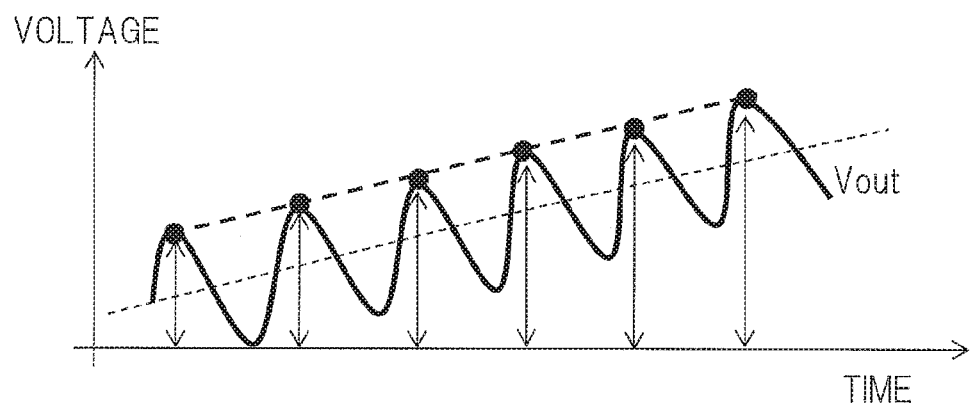
FIG. 9A is a waveform diagram of the output signal Vout when low frequency noise is added in the impedance measuring circuit in FIG. 1.

FIG. 9A is a waveform diagram of the output signal Vout when low frequency noise is added in the impedance measuring circuit 100 in FIG. 1. The low frequency noise is noise with a frequency lower than a frequency of the output signal Vout. In FIG. 9A, an amplitude of the output signal Vout is constant; however, a maximum value of the output signal Vout increases over time due to influence of the low frequency noise. Although not shown, thereafter, a maximum value of the output signal Vout decreases over time due to influence of the low frequency noise. The low frequency noise is attributable to flicker noise in the peak hold circuit 30 or noise occurring in the target 1 as a living body.

Figure 9B:
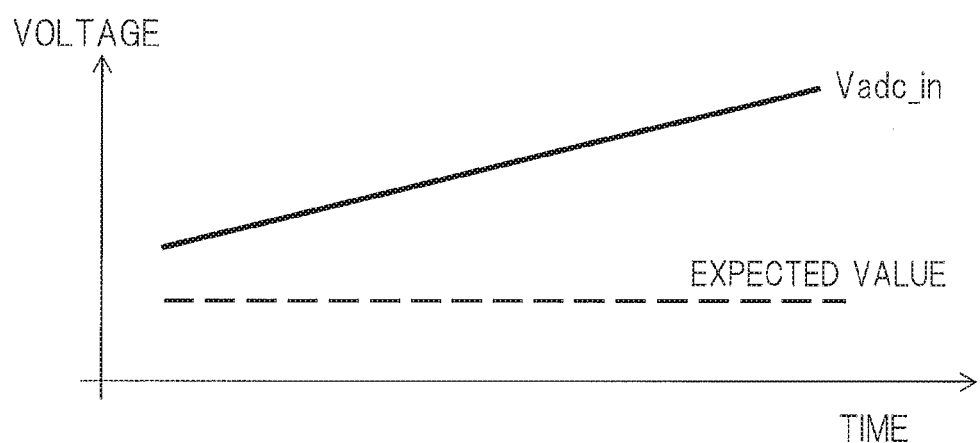
FIG. 9B is a waveform diagram of the hold value Vadc_in corresponding to FIG. 9A.

FIG. 9B is a waveform diagram of the hold value Vadc_in corresponding to FIG. 9A. The hold value Vadc_in increases over time. Assuming that the low frequency noise does not exist, the hold value Vadc_in is expected to be a constant value (expected value) regardless of time elapsed since an amplitude of the output signal Vout is constant. Therefore, a calculated impedance Z includes an error due to the low frequency noise.

In a third embodiment described below, such influence of the low frequency noise is suppressed.

(Third Embodiment)

A third embodiment is different from the first embodiment in a point that a maximum value and minimum value are held as peak values.

Figure 10:
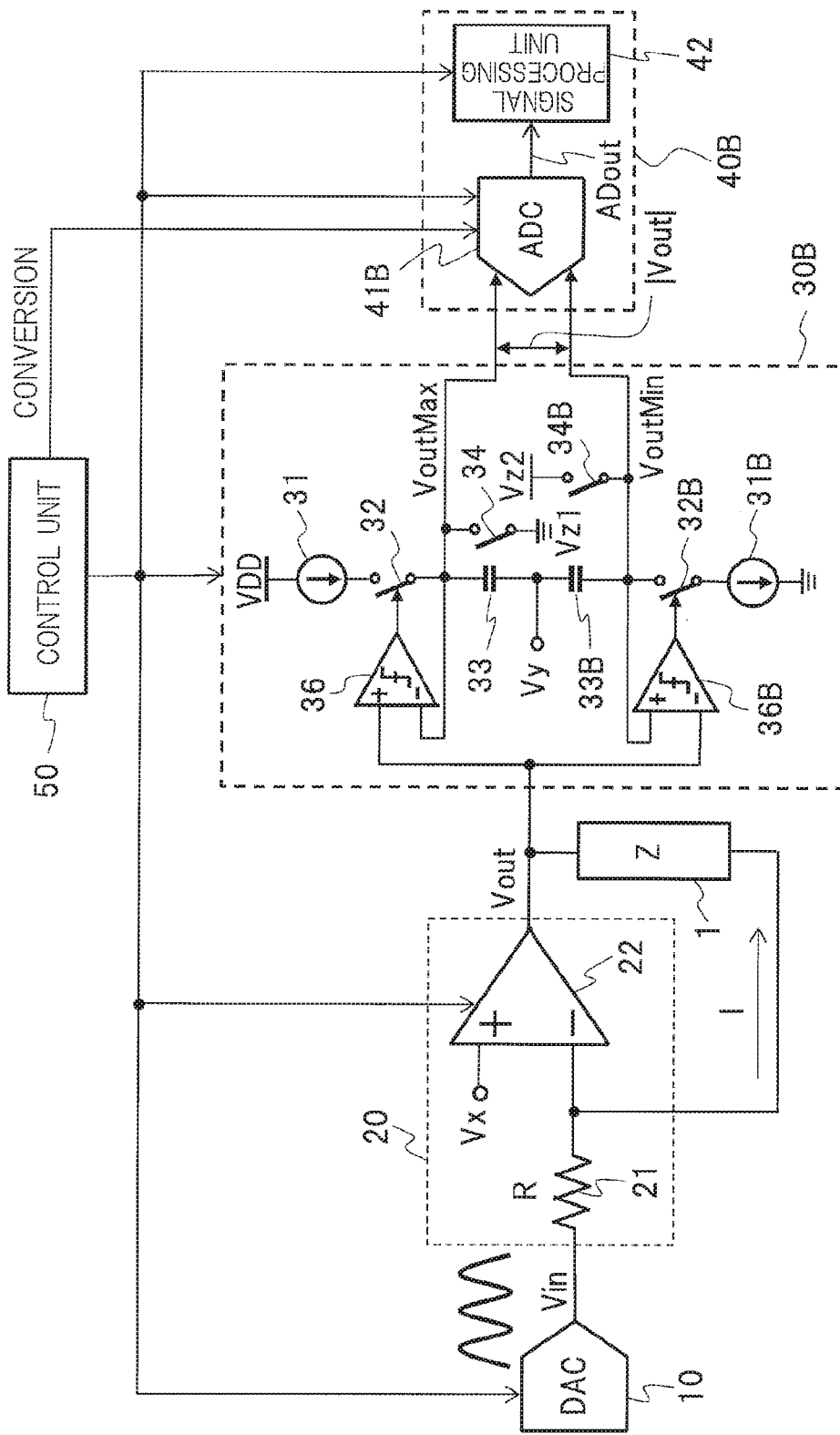
FIG. 10 is a block diagram illustrating an impedance measuring circuit according to a third embodiment.

FIG. 10 is a block diagram illustrating an impedance measuring circuit 100B according to the third embodiment. In FIG. 10, components common to those in FIG. 1 are denoted with the same signs as in FIG. 1. Different points are mainly described below. In the impedance measuring circuit 100B, a peak hold circuit 30B and an impedance calculation circuit 40B are different as compared to the first embodiment.

The peak hold circuit 30B holds a maximum value of an output signal Vout and outputs a maximum hold value VoutMax while holding a minimum value of the output signal Vout and outputs a minimum hold value VoutMin.

The peak hold circuit 30B includes, in addition to the configuration in FIG. 2A, a second current source 31B, a second switch 32B, a second capacitor element 33B, a reset switch 34B, and a second comparator 36B. Those elements including the second current source 31B form a negative peak hold circuit. That is, the peak hold circuit 30B includes a positive peak hold circuit and a negative peak hold circuit. Also, the amplifier 35 is not included and a voltage in one end of a first capacitor element 33 is output as the maximum hold value VoutMax, which are points different from FIG. 2A.

The second capacitor element 33B includes one end supplied with a first voltage Vy and another end for holding the minimum value of the output signal Vout. The minimum value held at the other end of the second capacitor element 33B is output as the minimum hold value VoutMin.

The second switch 32B includes one end connected to the other end of the second capacitor element 33B.

The second current source 31B imports a constant second current from another end of the second switch 32B to ground.

The reset switch 34B includes one end supplied with a voltage Vz2 and the other end connected to the other end of the second capacitor element 33B.

The voltage Vz2 is higher than an assumed maximum value of the minimum value of the output signal Vout. As a result, the reset switch 34B is turned on and a voltage in the other end of the second capacitor element 33B is initialized to the voltage Vz2. Thereafter, the second capacitor element 33B can hold a minimum value of the output signal Vout even when the minimum value is an assumed maximum value.

The second comparator 36B turns on the second switch 32B when the output signal Vout is smaller than or equal to the minimum hold value VoutMin. As a result, the second capacitor element 33B is discharged by the second current. The second comparator 36B turns off the second switch 32B when the output signal Vout is larger than the minimum hold value VoutMin. As a result, discharging of the second capacitor element 33B is halted. Therefore, when the minimum value of the output signal Vout decreases, the minimum hold value VoutMin decreases and is renewed.

The impedance calculation circuit 40B includes an AD converter 41B for performing AD conversion with a difference between the maximum hold value VoutMax and the minimum hold value VoutMin held in the peak hold circuit 30B. This allows the impedance calculation circuit 40B to calculate the impedance Z based on the difference between the maximum hold value VoutMax and the minimum hold value VoutMin.

Figure 11:
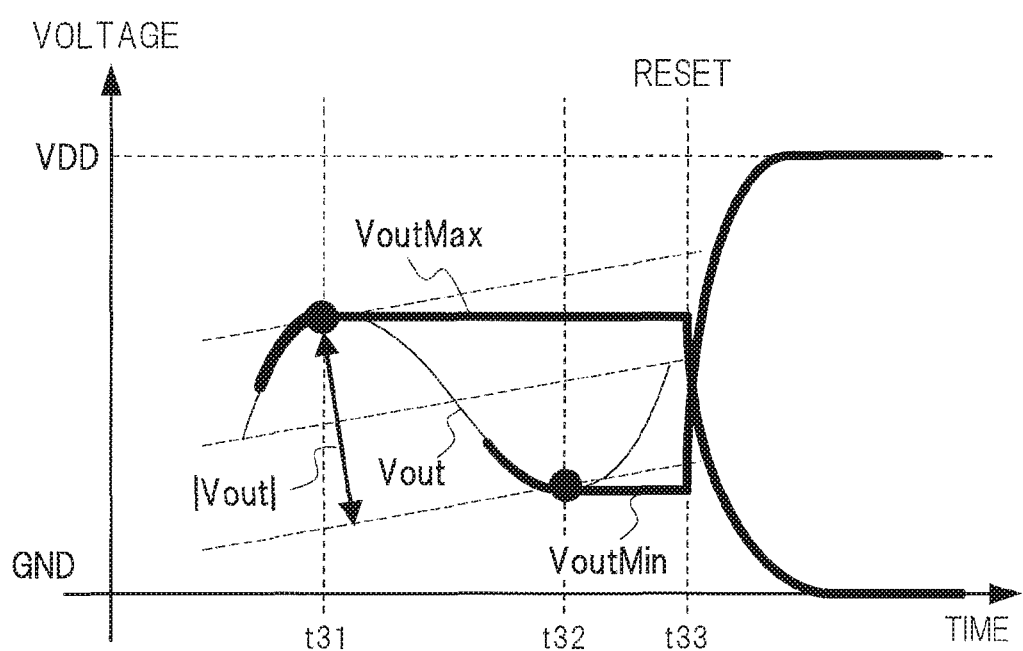
FIG. 11 is a waveform diagram of the output signal Vout, maximum hold value VoutMax, and minimum hold value VoutMin when low frequency noise is added in the impedance measuring circuit in FIG. 10.

FIG. 11 is a waveform diagram of the output signal Vout, maximum hold value VoutMax, and minimum hold value VoutMin when the low frequency noise is added in the impedance measuring circuit 100B in FIG. 10.

At a time t31, a maximum value of the output signal Vout is held as the maximum hold value VoutMax. At a time t32, a minimum value of the output signal Vout is held as the minimum hold value VoutMin. From the time t32 on, the difference between the maximum hold value VoutMax and the minimum hold value VoutMin does not include the low frequency noise and becomes a value corresponding to an amplitude of the output signal Vout. Therefore, the impedance Z can be calculated accurately. At a time t33, the maximum hold value VoutMax and the minimum hold value VoutMin are reset. In this example, the voltage Vz2 is a power supply voltage VDD while a voltage Vz1 is a ground voltage.

In this manner, since the impedance Z is calculated based on the difference between the maximum hold value VoutMax and the minimum hold value VoutMin according to the present embodiment, the impedance Z can be calculated while influence of the low frequency noise included in the output signal Vout is suppressed.

Incidentally, similarly to the second embodiment, a maximum value having been held may be subjected to the sample-hold and be output as the maximum hold value VoutMax while holding, and a minimum value having been held may be subjected to the sample-hold and be output as the minimum hold value VoutMin.

Note that the circuit configuration of the peak hold circuit 30B is a mere example and thus another configuration such as a configuration based on FIG. 2B may be used.

(Fourth Embodiment)

A fourth embodiment relates to another configuration of a peak hold circuit according to the third embodiment.

Figure 12:
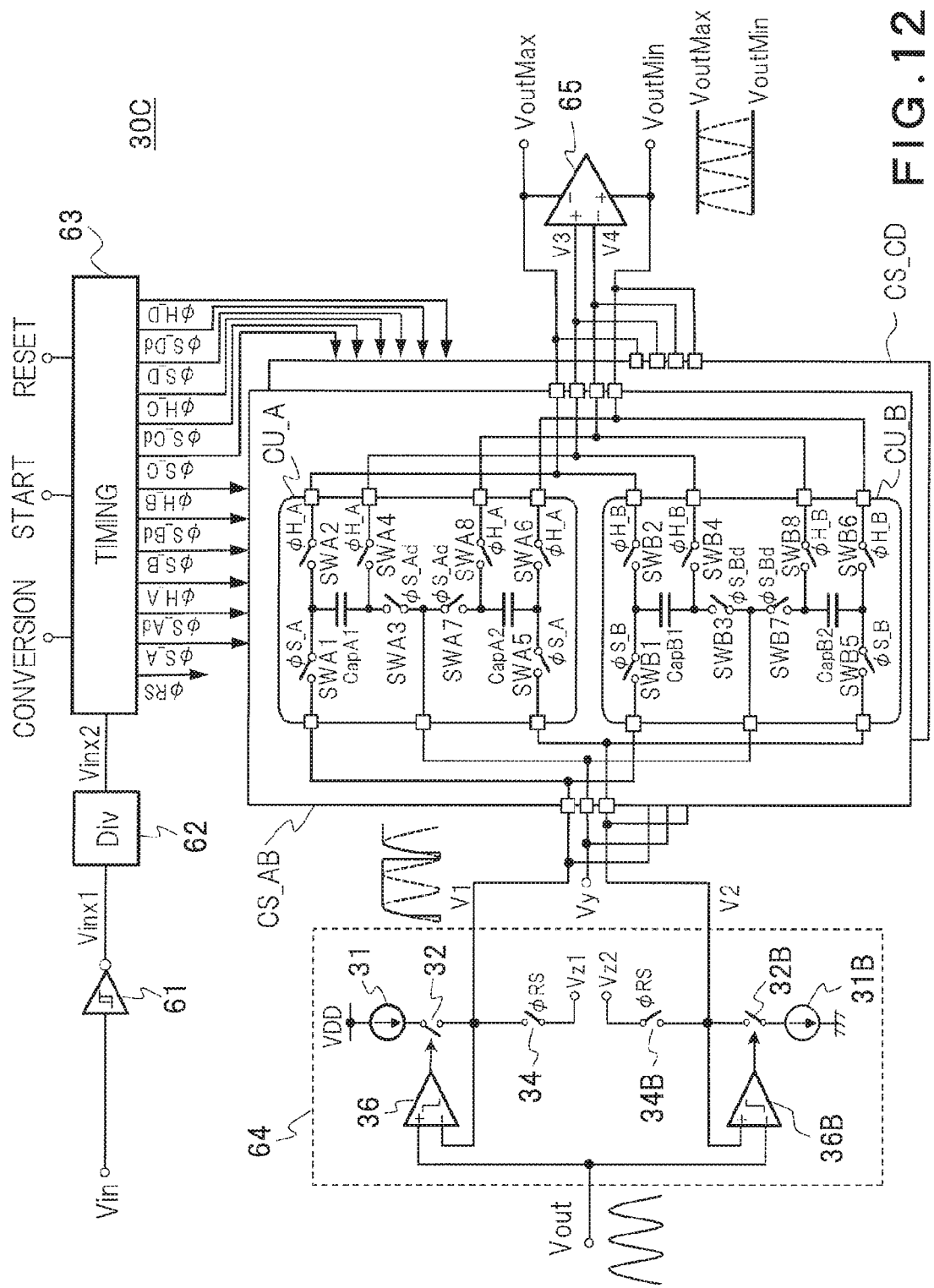
FIG. 12 is a circuit diagram illustrating a configuration of a peak hold circuit according to a fourth embodiment.

FIG. 12 is a circuit diagram illustrating a configuration of a peak hold circuit 30C according to a fourth embodiment. The peak hold circuit 30C conducts sample-hold of a maximum value having been held and outputs as a maximum hold value VoutMax while holding, and conducts sample-hold of a minimum value having been held and outputs as the minimum hold value VoutMin.

The peak hold circuit 30C includes a hysteresis buffer 61, a frequency divider 62, a timing signal generating circuit 63, a current source circuit 64, a first capacitor set CS_AB, a second capacitor set CS_CD, and a differential amplifier 65.

The first capacitor set CS_AB includes a first capacitor unit CU_A and a second capacitor unit CU_B.

Figure 13:
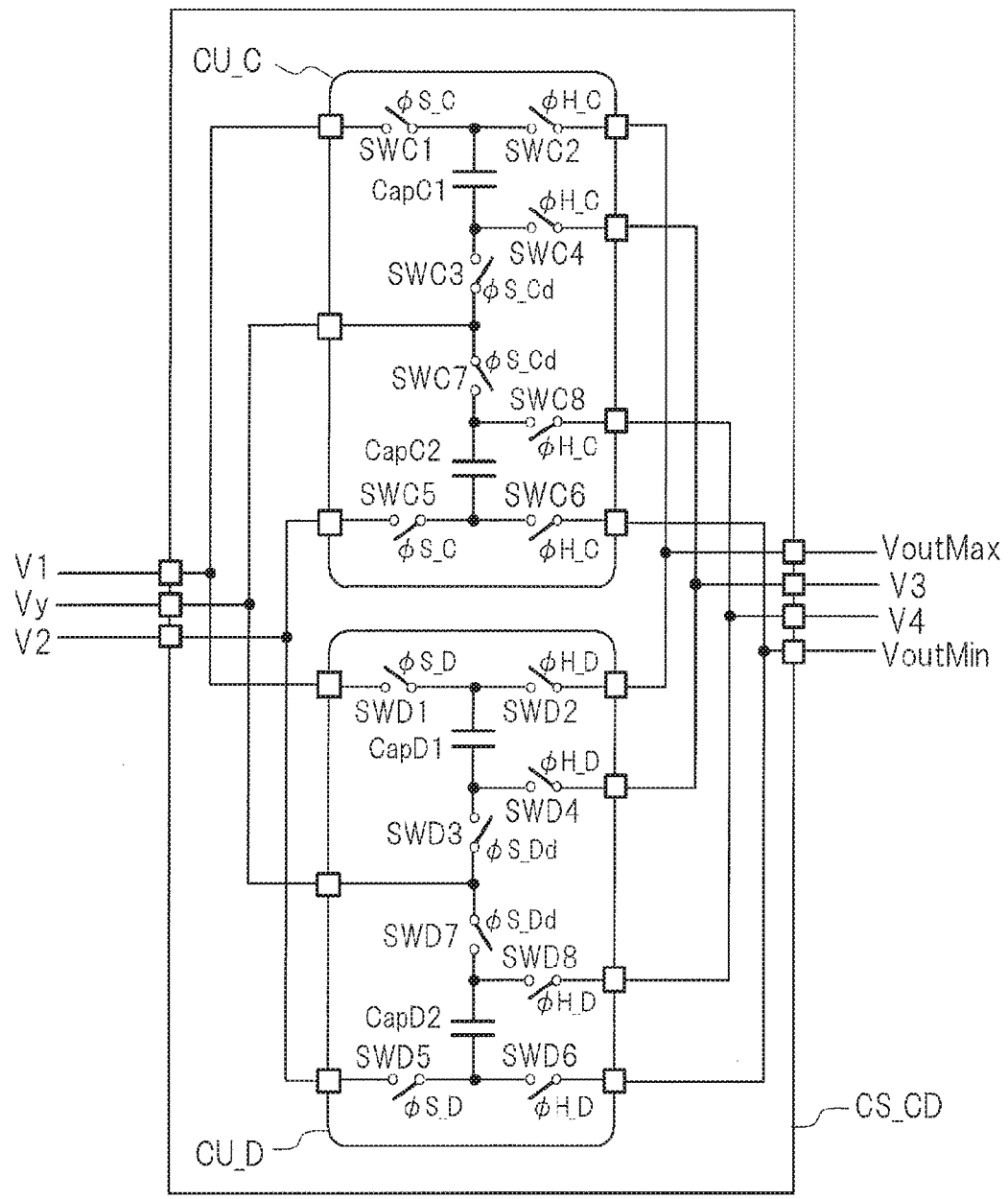
FIG. 13 is a circuit diagram illustrating a configuration of a second capacitor set in FIG. 12.

FIG. 13 is a circuit diagram illustrating a configuration of a second capacitor set CS_CD in FIG. 12. The second capacitor set CS_CD includes a third capacitor unit CU_C and a fourth capacitor unit CU_D.

The first capacitor set CS_AB and the second capacitor set CS_CD operate in a complementary manner.

The hysteresis buffer 61 is input with an input signal Vin and outputs a signal Vinx1 of a rectangular wave with a frequency same as that of the input signal Vin. The hysteresis buffer 61 may be input with an output signal Vout instead of the input signal Vin. However, when a target 1 is a living body, the output signal Vout is often attenuated from the input signal Vin and thus it is preferable that the input signal Vin is input.

The frequency divider 62 divides the signal Vinx1 into, for example, halves and outputs a signal Vinx2. The number of division is determined according to a peak hold cycle T, which will be described later.

The timing signal generating circuit 63 generates timing signals φRS, φS_A, φS_Ad, φH_A, φS_B, φS_Bd, φH_B, φS_C, φS_Cd, φH_C, φS_C, φS_Cd, and φH_C synchronized with the input signal Vin based on the signal Vinx2.

The current source circuit 64 includes a configuration of the peak hold circuit 30B in FIG. 10 excluding the first capacitor element 33 and second capacitor element 33B.

The first capacitor unit CU_A includes a first capacitor element CapA1, a second capacitor element CapA2, and switches SWA1 to SWA8 and is caused to switch between a peak hold state and a floating state based on the timing signals φS_A, φS_Ad, and φH_A. The first capacitor unit CU_A holds a maximum value of the output signal Vout in the first capacitor element CapA1 while holding a minimum value thereof in the second capacitor element CapA2 in the peak hold state and causes the first capacitor element CapA1 and second capacitor element CapA2 to float in the floating state.

The switch SWA1 includes one end connected to another end of a first switch 32 of the current source circuit 64 and another end connected to one end of the first capacitor element CapA1 and is on/off controlled with the timing signal φS_A.

The switch SWA2 includes one end connected to the one end of the first capacitor element CapA1 and another end connected to an inverting output terminal of the differential amplifier 65 and is on/off controlled with the timing signal φH_A.

The switch SWA3 includes one end supplied with a first voltage Vy and another end connected to another end of the first capacitor element CapA1 and is on/off controlled with the timing signal φS_Ad.

The switch SWA4 includes one end connected to the other end of the first capacitor element CapA1 and another end connected to a non-inverting input terminal of the differential amplifier 65 and is on/off controlled with the timing signal φH_A.

The switch SWA5 includes one end connected to one end of a second switch 32B of the current source circuit 64 and another end connected to one end of the second capacitor element CapA2 and is on/off controlled with the timing signal φS_A.

The switch SWA6 includes one end connected to the one end of the second capacitor element CapA2 and another end connected to a non-inverting output terminal of the differential amplifier 65 and is on/off controlled with the timing signal φH_A.

The switch SWA7 includes one end supplied with the first voltage Vy and another end connected to another end of the second capacitor element CapA2 and is on/off controlled with the timing signal φS_Ad.

The switch SWAB includes one end connected to the other end of the second capacitor element CapA2 and another end connected to an inverting input terminal of the differential amplifier 65 and is on/off controlled with the timing signal φH_A.

The second capacitor unit CU_B includes a third capacitor element CapB1, a fourth capacitor element CapB2, and switches SWB1 to SWB8 and is caused to switch between the peak hold state and the floating state based on the timing signals φS_B, φS_Bd, and φH_B. The second capacitor unit CU_B holds a maximum value in the third capacitor element CapB1 while holding a minimum value in the fourth capacitor element CapB2 in the peak hold state and causes the third capacitor element CapB1 and fourth capacitor element CapB2 to float in the floating state.

The third capacitor unit CU_C includes a fifth capacitor element CapC1, a sixth capacitor element CapC2, and switches SWC1 to SWC8 and is caused to switch between the peak hold state and the floating state based on the timing signals φS_C, φS_Cd, and φH_C. The third capacitor unit CU_C holds a maximum value in the fifth capacitor element CapC1 while holding a minimum value in the sixth capacitor element CapC2 in the peak hold state and causes the fifth capacitor element CapC1 and sixth capacitor element CapC2 to float in the floating state.

The fourth capacitor unit CU_D includes a seventh capacitor element CapD1, an eighth capacitor element CapD2, and switches SWD1 to SWD8 and is caused to switch between the peak hold state and the floating state based on the timing signals φS_D, φS_Dd, and φH_D. The fourth capacitor unit CU_D holds a maximum value in the seventh capacitor element CapD1 while holding a minimum value in the eighth capacitor element CapD2 in the peak hold state and causes the seventh capacitor element CapD1 and eighth capacitor element CapD2 to float in the floating state.

Connections among the respective elements in the second to fourth capacitor units CU_B, CU_C, and CU_D are in common with those in the first capacitor unit CU_A. Therefore, descriptions thereon are omitted.

Figure 14:
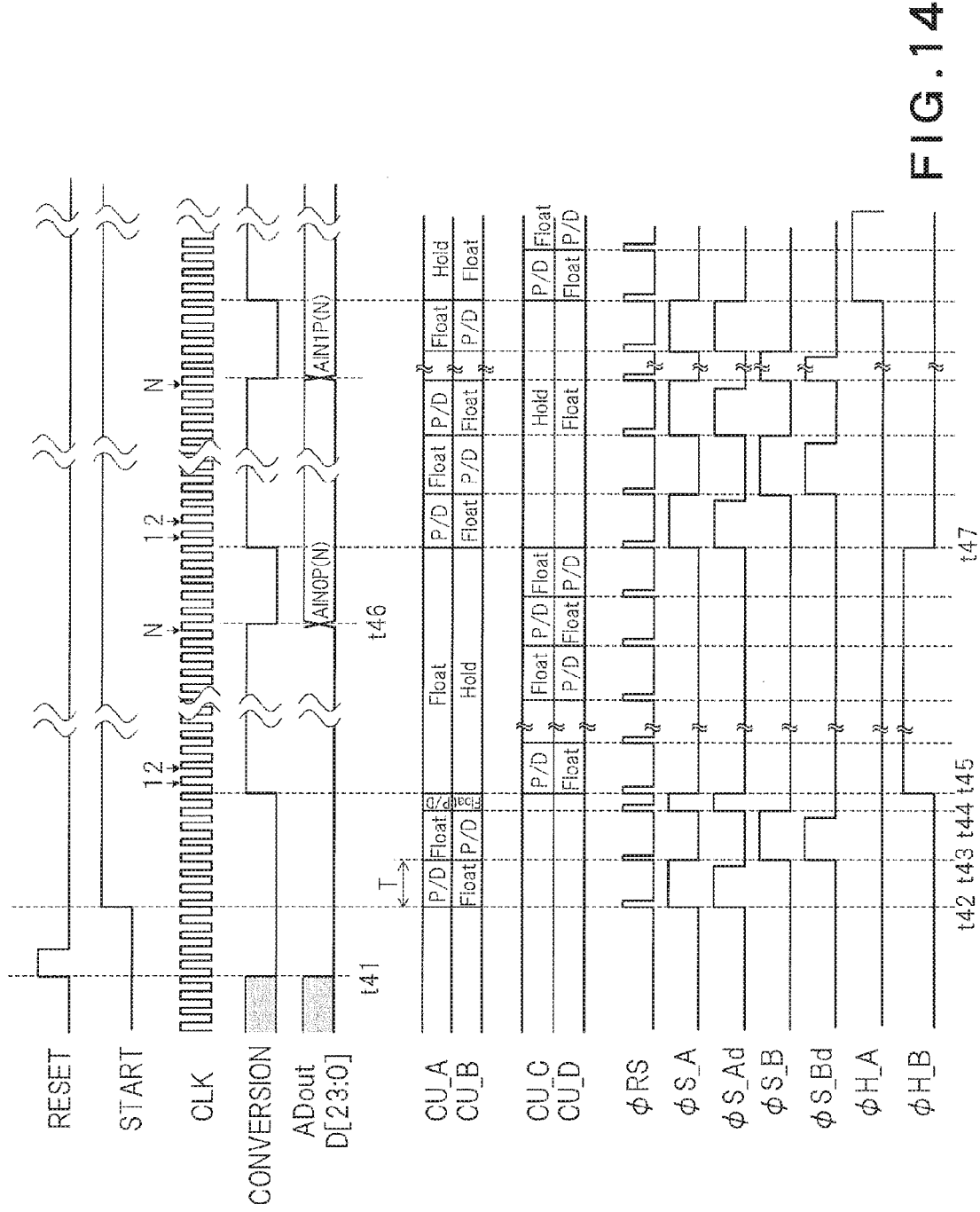
FIG. 14 is a timing chart illustrating respective signals in the peak hold circuit in FIG. 12.

FIG. 14 is a timing chart illustrating respective signals of the peak hold circuit 30C in FIG. 12.

First, at a time t41, a reset signal RESET becomes a high level for a certain period and the timing signal generating circuit 63 is reset for the certain period.

Next, at a time t42, a peak hold start signal START changes from a low level to a high level. This allows for the timing signal generating circuit 63 to cause the first capacitor unit CU_A and the second capacitor unit CU_B to switch alternately between the peak hold state (P/D) and floating state (Float) for every predetermined peak hold cycle T. Also, the timing signal generating circuit 63 resets (initializes) an element to be switched to the peak hold state from among the first to fourth capacitor units CU_A to CU_D.

In the example of FIG. 14, at the time t42, the timing signal generating circuit 63 causes the first capacitor unit CU_A to switch to the peak hold state and to be reset for a certain period and causes the second capacitor unit CU_B to switch to the floating state.

Figure 15A:
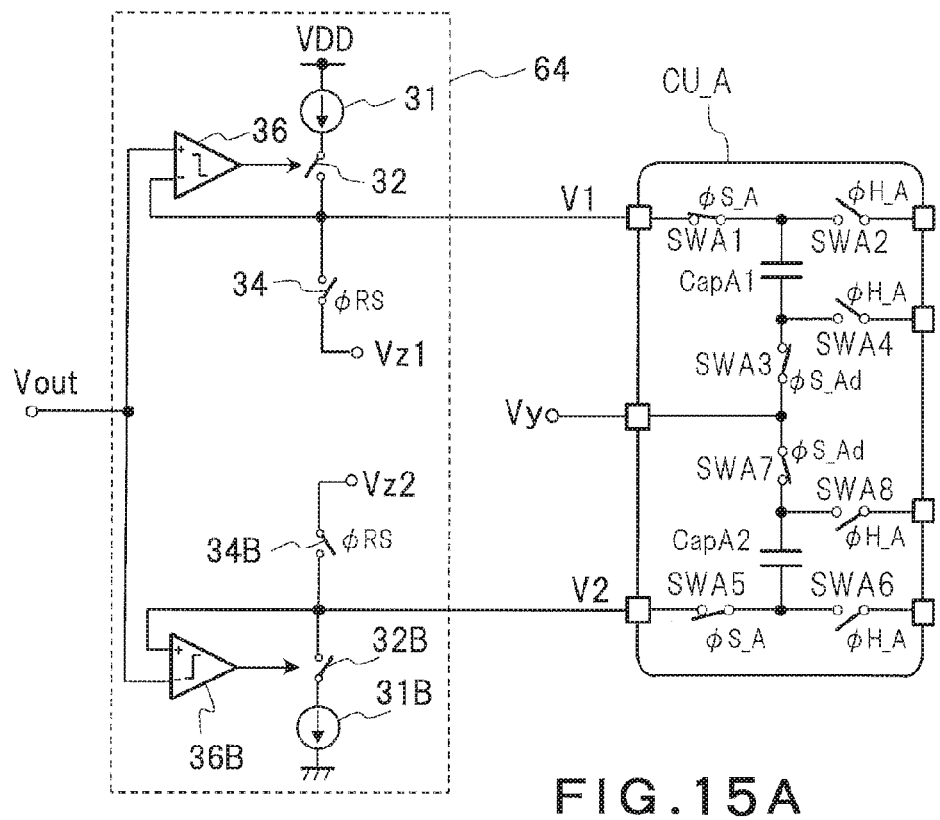
FIG. 15A is a diagram explaining a state of switches in a first capacitor unit in a peak hold state.

FIG. 15A is a diagram explaining a state of switches SWA1 to SWA8 of the first capacitor unit CU_A in the peak hold state. When the timing signals φS_A and φS_Ad become high levels at the time t42, the switches SWA1, SWA3, SWA5, and SWA7 are turned on. The timing signal φH_A stays at a low level and thus the switches SWA2, SWA4, SWA6, and SWA8 stay turned off. This allows one end of each of the first capacitor element CapA1 and second capacitor element CapA2 to be connected to the current source circuit 64 and another end thereof to be supplied with the first voltage Vy. That is, a similar circuit to the peak hold circuit 30B in FIG. 10 is configured.

Here, at the time t42, the timing signal φRS becomes a high level for a certain period. This allows the switches 34 and 34B of the current source circuit 64 to be turned on for the certain period. As a result, the first capacitor element CapA1 and second capacitor element CapA2 are reset.

The current source circuit 64 supplies a first current when the output signal Vout is larger than or equal to the maximum value and imports a second current when the output signal Vout is smaller than or equal to the minimum value. In this example, the maximum value is held in the first capacitor element CapA1 and the minimum value is held in the second capacitor element CapA2.

The timing signal generating circuit 63 causes the current source circuit 64 to supply the first current to the first, third, fifth, or seventh capacitor element CapA1, CapB1, CapC1, or CapD1 which is in the peak hold state from among the first to fourth capacitor units CU_A to CU_D. In this example, therefore, the current source circuit 64 supplies the first current to the first capacitor element CapA1 in the first capacitor unit CU_A.

The timing signal generating circuit 63 causes the current source circuit 64 to import the second current from the second, fourth, sixth, or eighth capacitor element CapA2, CapB2, CapC2, or CapD2 which is in the peak hold state from among the first to fourth capacitor units CU_A to CU_D. In this example, therefore, the current source circuit 64 imports the second current from the second capacitor element CapA2 in the first capacitor unit CU_A.

As a result, similarly to the peak hold circuit 30B in FIG. 10, the maximum value and minimum value of the output signal Vout are held in the first capacitor unit CU_A.

On the other hand, the timing signals φS_B, φS_Bd, and φH_B stays at a low level and thus the switches SWB1 to SWB8 stay turned off. Therefore, the third and fourth capacitor elements CapB1 and CapB2 in the second capacitor unit CU_B are floating.

At a time t43 when the peak hold cycle T has elapsed after the time t42, the timing signal generating circuit 63 causes the first capacitor unit CU_A to switch to the floating state, causes the second capacitor unit CU_B to switch to the peak hold state and to be reset for a certain period. Here, the timing signal generating circuit 63 changes the timing signal φS_Ad to a low level before the time t43 and changes the timing signal φS_A to a low level at the time t43. This allows for suppressing charge injection. Also, the timing signal generating circuit 63 changes the timing signals φS_B and φS_Bd to a high level at the time t43.

Preferably, the peak hold cycle T is twice or more a cycle of the input signal Vin. More preferably, the peak hold cycle T is twice the cycle of the input signal Vin. In this manner, even when the output signal Vout reaches a maximum value or minimum value during reset and the maximum value or minimum value cannot be held as peaks, a maximum value or minimum value in a subsequent cycle can be held as peaks.

Similarly, at a time t44 when the peak hold cycle T has elapsed after the time t43, the timing signal generating circuit 63 causes the first capacitor unit CU_A to switch to the peak hold state and to be reset for a certain period, and causes the second capacitor unit CU_B to switch to the floating state.

Next, at a time t45 before the peak hold cycle T elapses from the time t44, an AD conversion signal CONVERSION is changed from a low level to a high level (an AD conversion command is given). The AD conversion signal CONVERSION is asynchronous with the input signal Vin.

When the AD conversion command is given, the timing signal generating circuit 63 causes the first and second capacitor elements CapA1 and CapA2 or the third and fourth capacitor elements CapB1 and CapB2 which are in the floating state from among the first and second capacitor units CU_A and CU_B to be connected to the differential amplifier 65 and thereby conducting the sample-hold of the maximum value and minimum value having been held by the differential amplifier 65 (sample hold state (Hold)).

Also, when the AD conversion command is given, the timing signal generating circuit 63 causes an element which is in the peak hold state from among the first and second capacitor units CU_A and CU_B to switch to the floating state.

Furthermore, when the AD conversion command is given, the timing signal generating circuit 63 causes the third and fourth capacitor units CU_C and CU_D to switch alternately between the peak hold state and floating state for every peak hold cycle T.

In the example illustrated, at the time t45, the second capacitor unit CU_B is in the floating state. Therefore, the third and fourth capacitor elements CapB1 and CapB2 in the second capacitor unit CU_B are connected to the differential amplifier 65 and the first capacitor unit CU_A is switched to the floating state.

Figure 15B:
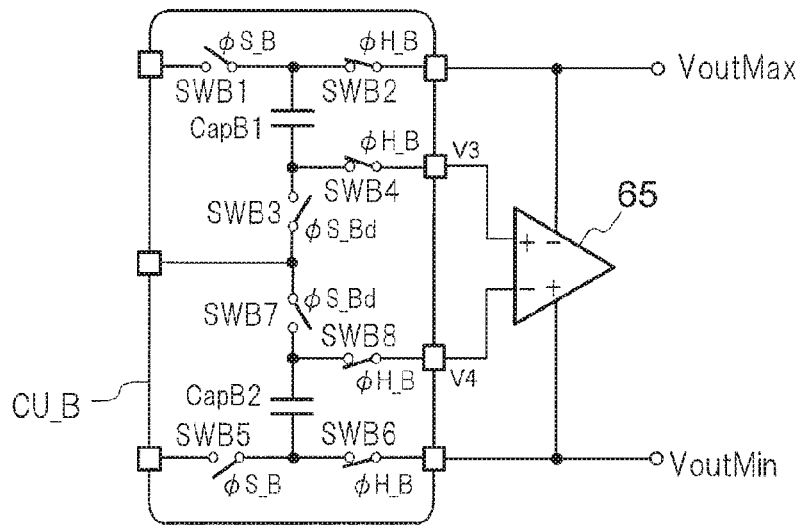
FIG. 15B is a diagram explaining a state of switches in a second capacitor unit in a sample hold state.

FIG. 15B is a diagram explaining a state of the switches SWB1 to SWB8 in the second capacitor unit CU_B in the sample hold state. The timing signals φS_A and φS_Ad become a low level while the timing signal φH_B becomes a high level at the time t45. The timing signals φS_B, φS_Bd, and φH_A stays at a low level. Therefore, the switches SWA1 to SWA8 are turned off. Also, the switches SWB2, SWB4, SWB6, and SWB8 are turned on while the switches SWB1, SWB3, SWB5, and SWB7 stay turned off. As a result, one end of the third capacitor element CapB1 is connected to the non-inverting input terminal of the differential amplifier 65 while another end thereof is connected to the inverting output terminal of the differential amplifier 65. One end of the fourth capacitor element CapB2 is connected to the non-inverting input terminal of the differential amplifier 65 while another end thereof is connected to the non-inverting output terminal of the differential amplifier 65. This allows the maximum value and minimum value held in the third and fourth capacitor elements CapB1 and CapB2 are held in the differential amplifier 65 as samples.

The AD converter 41B, having received the AD conversion command, performs AD conversion of the value held as a sample in synchronization with a clock signal CLK supplied to the AD converter 41B. In the example illustrated, at a timing (time t46) when the clock signal CLK reaches N clocks after the time t45, the AD conversion signal CONVERSION changes to a low level and the AD converter 41B outputs a digital value ADout=AINOP (N).

Next, at a time t47, the AD conversion signal CONVERSION is again changed from a low level to a high level and a subsequent AD conversion command is given. When a subsequent AD conversion command is given, the timing signal generating circuit 63 causes the first and second capacitor units CU_A and CU_B to switch alternately between the peak hold state and floating state for every peak hold cycle T, causes the fifth and sixth capacitor elements CapC1 and CapC2 or the seventh and eighth capacitor elements CapD1 and CapD2 which are in the floating state from among the third and fourth capacitor units CU_C and CU_D to be connected to the differential amplifier 65, and thereby causing the maximum value and minimum value having been held to be held as samples in the differential amplifier 65.

The above operations are repeated and thereby AD conversion is sequentially performed.

In this manner, every time the AD conversion command is given, the first and second capacitor units CU_A and CU_B switch alternately between a first state where the peak hold state and floating state are repeated alternately and a second state where one is in the sample hold state and the other is in the floating state.

Every time the AD conversion command is given, the third and fourth capacitor units CU_C and CU_D switch alternately between a third state, where the peak hold state and floating state are alternately repeated while the first and second capacitor units CU_A and CU_B are in the second state, and a fourth state, where one of the units is in the sample hold state and the other is in the floating state while the first and second capacitor units CU_A and CU_B are in the first state.

Incidentally, a specific configuration of the current source circuit 64 is not specifically limited. An example of preferable configuration will be described below.

Figure 16:
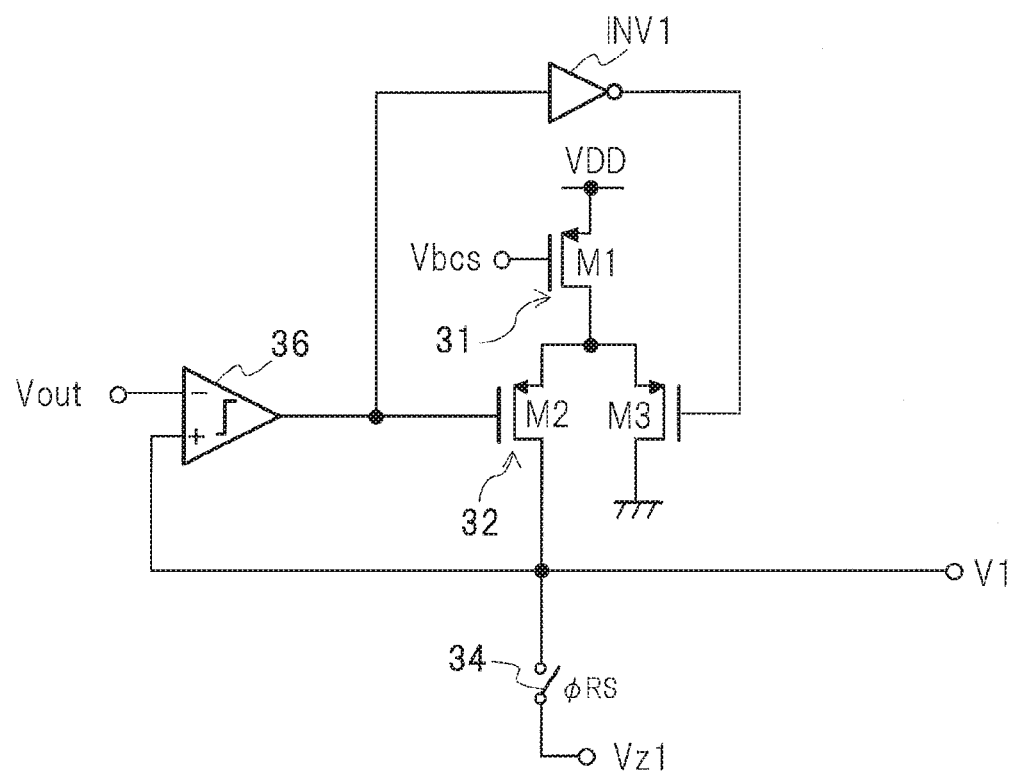
FIG. 16 is a detailed circuit diagram of a part of a current source circuit in FIG. 12.

FIG. 16 is a detailed circuit diagram of a part of the current source circuit 64 in FIG. 12. In FIG. 16, components common to those in FIG. 12 are denoted with the same signs as in FIG. 12. Different points are mainly described below.

The current source circuit 64 includes a PMOS transistor M1 as a first current source 31 and includes a PMOS transistor M2 as the first switch 32. The current source circuit 64 further includes a PMOS transistor M3 and an inverter INV1, which is a point different from FIG. 12.

The PMOS transistor M1 includes a source supplied with a power supply voltage VDD and a gate supplied with a predetermined bias voltage Vbcs.

The PMOS transistor M2 includes a source connected to a drain of the PMOS transistor M1, a gate connected to an output terminal of the first comparator 36, and a drain connected to a non-inverting input terminal of the first comparator 36.

The PMOS transistor M3 includes a source connected to the drain of the PMOS transistor M1 and a drain connected to ground.

The inverter INV1 inverts an output signal from the first comparator 36 and outputs the signal to a gate of the PMOS transistor M3. Therefore, the PMOS transistors M2 and M3 can switch alternately between on and off. That is, when the output signal from the first comparator 36 is at a high level, the PMOS transistor M2 is turned off while the PMOS transistor M3 is turned on. When the output signal from the first comparator 36 is at a low level, the PMOS transistor M2 is turned on while the PMOS transistor M3 is turned off.

Therefore, the PMOS transistor M1 continues to send the first current regardless of the output signal from the first comparator 36. Thus, as compared to a case where the PMOS transistor M3 is not included, it is possible to switch between, in a speedy manner, whether the current source circuit 64 supplies the first current. Therefore, the present embodiment is also preferable when the output signal from the first comparator 36 switches in a speedy manner.

Although not shown, a configuration for drawing the second current such as the second current source 31B and second switch 32B may be formed in a similar manner using NMOS transistors.

In this manner, according to the present embodiment, the first and second capacitor units CU_A and CU_B alternately repeats the peak hold state and floating state. As a result, even when the input signal Vin and AD conversion signal CONVERSION are asynchronous with each other, when the AD conversion command is given, a voltage value in the floating state reflecting the correct maximum value and minimum value can be subjected to AD conversion without subjecting to AD conversion a voltage value held as a peak which may be incorrect. A voltage value in the floating state is obtained by holding the output signal Vout of a preceding cycle as a peak and thus the value correctly reflects the maximum value and minimum value of the output signal Vout. Therefore, the accurate impedance Z can be calculated.

Also, the third and fourth capacitor units CU_C and CU_D are further included and thereby allowing the third and fourth capacitor units CU_C and CU_D to alternately repeat the peak hold state and floating state when the first and second capacitor units CU_A and CU_B are used for AD conversion. This allows for holding the output signal Vout as a peak even during AD conversion. Therefore, subsequent AD conversion can be performed immediately after the present AD conversion. This allows for sequentially measuring changes in the amplitude of the output signal Vout. Therefore, a change in the impedance Z can be measured more accurately.

Incidentally, in the first to fourth embodiments, examples where the input signal Vin and output signal Vout are single phase signals have been described; however, the signals may be differential signals.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An impedance measuring circuit comprising:
   an amplification circuit connected to a target and to amplify a predetermined input signal with a gain corresponding to an impedance in the target and to output an output signal;
   a peak hold circuit to hold a peak value of the output signal and to output a hold value; and
   an impedance calculation circuit to calculate the impedance in the target based on the hold value,
   wherein the amplification circuit comprises:
   a resistor comprising one end supplied with the input signal; and
   a differential amplifier comprising a first input node connected to another end of the resistor, a second input node supplied with a reference voltage, and an output node to amplify a difference between a voltage in the first input node and the reference voltage and to output the output signal, and
   the target is connected between the first input node and the output node of the differential amplifier.

2. The impedance measuring circuit according to claim 1, wherein the input signal is an AC signal,
   the impedance calculation circuit comprises:

an AD converter to convert the hold value into a digital signal; and
a signal processing unit to calculate the impedance based on the digital signal,
a frequency of the AC signal being higher than a frequency that the AD converter can perform AD conversion with.

3. The impedance measuring circuit according to claim 1, wherein the peak value comprises a maximum value and a minimum value of the output signal,
the hold value comprises a maximum hold value and a minimum hold value, and
the impedance calculation circuit calculates the impedance based on a difference between the maximum hold value and the minimum hold value.

4. The impedance measuring circuit according to claim 1, wherein the peak hold circuit conducts sample-hold of the held peak value and outputs a sample-hold value as the hold value.

5. An impedance measuring circuit comprising:
an amplification circuit connected to a target and to amplify a predetermined input signal with a gain corresponding to an impedance in the target and to output an output signal;
a peak hold circuit to hold a peak value of the output signal and to output a hold value; and
an impedance calculation circuit to calculate the impedance in the target based on the hold value,
wherein the peak value comprises a maximum value of the output signal,
the hold value comprises a maximum hold value, and
the peak hold circuit comprises:
a first current source to output a first current;
a first switch supplied with the first current from one end thereof;
a first capacitor element, connected to another end of the first switch, the element comprising one end to output the maximum hold value and another end supplied with a first voltage; and
a first comparator to turn on the first switch when the output signal is larger than or equal to the maximum hold value and to turn off the first switch when the output signal is less than the maximum hold value.

6. The impedance measuring circuit according to claim 5, wherein the peak value comprises a minimum value of the output signal,
the hold value comprises a minimum hold value, and
the peak hold circuit comprises:
a second capacitor element comprising one end supplied with the first voltage and another end to output the minimum hold value;
a second switch comprising one end connected to the other end of the second capacitor element;
a second current source to import a second current from another end of the second switch; and
a second comparator to turn on the second switch when the output signal is smaller than or equal to the minimum hold value and to turn off the second switch when the output signal is larger than the minimum hold value.

7. An impedance measuring circuit comprising:
an amplification circuit connected to a target and to amplify a predetermined input signal with a gain corresponding to an impedance in the target and to output an output signal;
a peak hold circuit to hold a peak value of the output signal and to output a hold value; and
an impedance calculation circuit to calculate the impedance in the target based on the hold value,
wherein the peak value comprises a maximum value and a minimum value of the output signal,
the hold value comprises a maximum hold value and a minimum hold value, and
the impedance calculation circuit calculates the impedance based on a difference between the maximum hold value and the minimum hold value,
wherein the peak hold circuit comprises:
a timing signal generating circuit to generate a timing signal synchronized with the input signal;
a first capacitor unit comprising a first capacitor element and a second capacitor element and to be switched between a peak hold state and a floating state based on the timing signal, to hold the maximum value and the minimum value in the first capacitor element and the second capacitor element in the peak hold state, and to cause the first capacitor element and the second capacitor element to float in the floating state;
a second capacitor unit comprising a third capacitor element and a fourth capacitor element and to be switched between the peak hold state and the floating state based on the timing signal, to hold the maximum value and the minimum value in the third capacitor element and the fourth capacitor element in the peak hold state, and to cause the third capacitor element and the fourth capacitor element to float in the floating state; and
a differential amplifier, and
the timing signal generating circuit causes the first capacitor unit and the second capacitor unit to switch alternately between the peak hold state and the floating state for every predetermined peak hold cycle, and, when an AD conversion command is given, causes the first capacitor element and the second capacitor element or the third capacitor element and the fourth capacitor element which are in the floating state from among the first capacitor unit and the second capacitor unit to be connected to the differential amplifier, and causes the differential amplifier to conduct sample-hold of the held maximum value and the held minimum value as the maximum hold value and the minimum hold value.

8. The impedance measuring circuit according to claim 7, wherein the peak hold circuit comprises:
a third capacitor unit comprising a fifth capacitor element and a sixth capacitor element and to be switched between the peak hold state and the floating state based on the timing signal, to hold the maximum value and the minimum value in the fifth capacitor element and the sixth capacitor element in the peak hold state, and to cause the fifth capacitor element and the sixth capacitor element to float in the floating state; and
a fourth capacitor unit comprising a seventh capacitor element and an eighth capacitor element and to be switched between the peak hold state and the floating state based on the timing signal, to hold the maximum value and the minimum value in the seventh capacitor element and the eighth capacitor element in the peak hold state, and to cause the seventh capacitor element and the eighth capacitor element to float in the floating state, and
the timing signal generating circuit causes the third capacitor unit and the fourth capacitor unit to switch alternately between the peak hold state and the floating state for every peak hold cycle when the AD conversion command is given and, when the AD conversion command is subsequently given, causes the first capacitor unit and the second capacitor unit to switch alternately between the peak hold state and the floating state for every peak hold cycle, causes the fifth capacitor element and the sixth capacitor element or the seventh capacitor element and the eighth capacitor element which are in the floating state from among the third capacitor unit and the fourth capacitor unit to be connected to the differential amplifier, and causes the differential amplifier to conduct sample-hold of the held maximum value and the held minimum value as the maximum hold value and the minimum hold value.

9. The impedance measuring circuit according to claim 8, wherein the peak hold circuit comprises a current source circuit to supply a first current when the output signal is larger than or equal to the maximum value and to import a second current when the output signal is smaller than or equal to the minimum value, and the timing signal generating circuit causes the current source circuit to supply the first current to the first, third, fifth or seventh capacitor element which is in the peak hold state from among the first to fourth capacitor units and to import the second current from the second, fourth, sixth or eighth capacitor element which is in the peak hold state from among the first to fourth capacitor units.

\* \* \* \* \*